United States Patent
Hamada et al.

(10) Patent No.: US 7,187,773 B2
(45) Date of Patent: Mar. 6, 2007

(54) SYSTEM FOR EVALUATING ABNORMAL SOUND, SOUND RECORDER AND APPARATUS FOR EVALUATING ABNORMAL SOUND

(75) Inventors: Tsuyoshi Hamada, Osaka (JP); Nozomi Kusao, Osaka (JP); Michiaki Ogino, Osaka (JP); Masaru Ando, Osaka (JP); Ryoichi Edo, Osaka (JP)

(73) Assignee: Daihatsu Motor Co., Ltd. (JP)

( * ) Notice: Subject to any disclaimer, the term of this patent is extended or adjusted under 35 U.S.C. 154(b) by 9 days.

(21) Appl. No.: 10/415,369

(22) PCT Filed: Sep. 28, 2001

(86) PCT No.: PCT/JP01/08609

§ 371 (c)(1),
(2), (4) Date: Apr. 28, 2003

(87) PCT Pub. No.: WO02/44671

PCT Pub. Date: Jun. 6, 2002

(65) Prior Publication Data
US 2004/0015251 A1   Jan. 22, 2004

(30) Foreign Application Priority Data
Dec. 1, 2000   (JP)   ............... P2000-367589

(51) Int. Cl.
*H04R 29/00* (2006.01)
(52) U.S. Cl. ............... 381/56; 73/116; 73/587; 701/33; 702/183; 702/185
(58) Field of Classification Search .......... 381/56, 381/58, 86; 701/29, 33; 702/182–186; 73/587, 73/660, 659, 602, 649, 650, 589, 865.9, 116, 73/117.4, 119 R
See application file for complete search history.

(56) References Cited

U.S. PATENT DOCUMENTS

| | | | | |
|---|---|---|---|---|
| 3,657,922 | A | * | 4/1972 | Sibeud .................... 73/117.3 |
| 5,850,209 | A | * | 12/1998 | Lemke et al. ............... 345/156 |
| 5,932,801 | A | * | 8/1999 | Akishita et al. ............. 73/660 |
| 6,094,609 | A | * | 7/2000 | Arjomand .................. 701/29 |
| 6,169,943 | B1 | * | 1/2001 | Simon et al. ............... 701/29 |
| 6,175,787 | B1 | * | 1/2001 | Breed ...................... 701/29 |
| 6,360,607 | B1 | * | 3/2002 | Charette et al. ............ 73/587 |

(Continued)

FOREIGN PATENT DOCUMENTS

JP   62-148999 A   7/1987

(Continued)

*Primary Examiner*—Brian T. Pendleton
(74) *Attorney, Agent, or Firm*—Banner & Witcoff, Ltd.

(57) ABSTRACT

An abnormal sound evaluation system according to this invention includes a sound recording device for recording a sound generated from equipment at a location adjacent the equipment, and an abnormal sound evaluation device for evaluating the sound recorded, wherein: the sound recording device includes sound data conversion means for converting the recorded sound into digital sound data, and sound data output means for outputting the digital sound data thus converted for the abnormal sound evaluation device; and the abnormal sound evaluation device includes sound data input means for receiving the digital sound data, and abnormal sound evaluation means for evaluating the sound as to abnormality based on the digital sound data inputted and outputting a conclusion of the evaluation including abnormality information about the equipment.

9 Claims, 3 Drawing Sheets

U.S. PATENT DOCUMENTS

| | | | | |
|---|---|---|---|---|
| 6,486,678 B1 * | 11/2002 | Spears | ......................... | 324/555 |
| 6,489,884 B1 * | 12/2002 | Lamberson et al. | .......... | 73/660 |
| 6,507,790 B1 * | 1/2003 | Radomski | .................... | 702/39 |
| 6,637,267 B2 * | 10/2003 | Fiebelkorn et al. | ............ | 73/587 |
| 6,718,239 B2 * | 4/2004 | Rayner | ........................ | 701/35 |
| 6,721,640 B2 * | 4/2004 | Glenn et al. | ................... | 701/35 |
| 6,782,345 B1 * | 8/2004 | Siegel et al. | ................ | 702/183 |
| 6,845,161 B2 * | 1/2005 | Boss | ............................ | 381/56 |

FOREIGN PATENT DOCUMENTS

| | | |
|---|---|---|
| JP | 04-363641 | 12/1992 |
| JP | 11-083618 A | 3/1999 |
| JP | 11-278041 | 10/1999 |

\* cited by examiner

Fig.4

CONCLUSION OF EVALUATION

| | |
|---|---|
| 1. Presence or absence of abnormality | Present |
| 2. Location of abnormality | Exhaust valve |
| 3. Abnormality condition | Wear or crack |
| 4. Whether repair is required | Required |
| 5. Replacement part | Valve seat |

SYSTEM FOR EVALUATING ABNORMAL SOUND, SOUND RECORDER AND APPARATUS FOR EVALUATING ABNORMAL SOUND

CROSS REFERENCE TO RELATED APPLICATIONS

This is a U.S. National Phase Application under 35 U.S.C. § 371 and applicant herewith claims the benefit of priority of PCT/JP01/08609 filed Sep. 28, 2001, which was published Under PCT Article 21(2), which claims priority to Japanese Application No. P2000-367589, filed Dec. 1, 2000, the entire contents of which are incorporated herein by reference.

TECHNICAL FIELD

The present invention relates to an abnormal sound evaluation system for evaluating an abnormal sound generated upon the occurrence of abnormality in equipment such as a vehicle or an engine on board of such a vehicle for example, and to a sound recording device and an abnormal sound evaluation device which are suitable for the system.

BACKGROUND ART

Heretofore, it has been a conventional practice that when an abnormality or failure occurs at, for example, an engine in a vehicle such as an automobile, such an abnormality or failure is evaluated from an abnormal sound generated by the engine. Usually, a technician visits, for example, a car dealer or a service garage to which the vehicle has been brought and conduct such abnormality evaluation based on abnormal sound by listening to an abnormal sound at that site. In such a case, if the evaluation cannot reach a conclusion, documents concerning abnormal sounds that have been so far collected are searched for the description of an abnormal sound substantially the same as the abnormal sound under evaluation to judge whether the sound in question is abnormal. Alternatively, if the abnormality judgment is impossible at the site, the vehicle is carried to a garage that is capable of examining the vehicle or to the manufacturer of the vehicle and subjected to a noise and vibration evaluation (NV evaluation) for investigation of the cause by analysis. When the cause of the abnormal sound is found out then a proper measure is taken. Since such judgment based on human's sensitivity may vary with different evaluators, a system for evaluation based on fixed criteria has been desired.

On the other hand, one known technique for evaluating abnormality of a production line based on sound is a technique such that sound data obtained from a motor actuator for use in a vehicle air conditioner is analyzed using plural characteristic volumes to determine the condition of the motor actuator from the conclusion of the analysis, as described in Japanese Patent Laid-Open Gazette No. HEI 11-278041 for example. Another known technique described in Japanese Patent Laid-Open Gazette No. HEI 4-363641 is to compare an engine sound generated at starting to a reference engine sound and judge whether the battery or the starter as well as the alternator is in an abnormal condition on the basis of the result of the comparison.

The aforementioned abnormality evaluation device is adapted to judge whether abnormality occurs or not at the site where the sound is recorded. Such an adaptation is convenient if the abnormality judgment is made in a factory before shipment. However, if a vehicle already shipped has abnormality, the abnormality evaluation device has to be transported to a site where the vehicle to be evaluated for abnormality is located. For this reason, if the abnormality evaluation device is up-scaled to accommodate a large volume of data as criteria for judgment for a higher precision, the convenience in transporting such an up-scaled device is sometimes lowered.

DISCLOSURE OF INVENTION

An object of the present invention is to eliminate such an inconvenience.

To attain such an object, the present invention provides the following means. That is, an abnormal sound evaluation system according to claim 1 is characterized by comprising a sound recording device for recording a sound generated from equipment at a location adjacent the equipment, and an abnormal sound evaluation device for evaluating the sound recorded, wherein: the sound recording device includes sound data conversion means for converting the recorded sound into digital sound data, and sound data output means for outputting the digital sound data thus converted for the abnormal sound evaluation device; and the abnormal sound evaluation device includes sound data input means for receiving the digital sound data, and abnormal sound evaluation means for evaluating the sound as to abnormality based on the digital sound data inputted and outputting a conclusion of the evaluation including abnormality information about the equipment.

The "equipment", as used in the present invention, is meant to include various vehicles such as an automobile, components included in such a vehicle such as an engine, transmission, suspension and differential gear, various machine tools constituting production equipment in a factory, construction machines, and various production plants.

The expression "outputting the digital sound data for the abnormal sound evaluation device", as used herein, is meant to include on-line outputting of the digital sound data to the abnormal sound evaluation device via a network such as Internet from a remote site or via an in-house network such as intranet, and off-line outputting of the digital sound data to the abnormal sound evaluation device by storing the digital sound data into a portable storage medium such as a floppy disk or a magneto-optical disk.

According to this construction, the sound recording device is operative to record a sound, convert the recorded sound into digital sound data and input the converted digital sound data to the abnormal sound evaluation device, and the abnormal sound evaluation device is operative to evaluate the sound as to whether the sound is abnormal or not based on the digital sound data. Since the sound recording device has the sound data output means for outputting the digital sound data converted from the sound for the abnormal sound evaluation device, the sound recording device and the abnormal sound evaluation device need not be located at a same site.

Thus, in the case where the equipment is the engine of a vehicle for example, it is possible to evaluate an abnormal sound even when the vehicle is at a standstill at a site other than the place where the abnormal sound evaluation device is installed, for example, on a highway. Further, since the abnormal sound evaluation device is capable of receiving digital sound data from plural sound recording devices, it is possible to avoid redundancy of functions thereby to reduce the cost to be incurred for the system as a whole.

An abnormal sound evaluation system according to claim 2 is characterized by comprising a sound recording device for recording a sound generated from equipment at a location adjacent the equipment, and an abnormal sound evaluation device for evaluating the sound recorded, wherein:

the sound recording device includes sound data conversion means for converting the recorded sound into digital sound data, sound data output means for outputting the digital sound data thus converted for the abnormal sound evaluation device, and evaluation conclusion input means for receiving a conclusion of evaluation outputted from the abnormal sound evaluation device; and the abnormal sound evaluation device includes sound data input means for receiving the digital sound data outputted from the sound recording device, abnormal sound evaluation means for evaluating the sound based on the digital sound data inputted and outputting a conclusion of the evaluation including abnormality information, and evaluation conclusion output means for outputting the conclusion of the evaluation outputted by the abnormal sound evaluation means for the sound recording device.

The expression "outputting the conclusion of the evaluation for the sound recording means", as used herein, is meant to include on-line outputting and off-line outputting, as in the former case.

In this construction, like the invention according to claim 1, the sound recording device is operative to convert a sound recorded into digital sound data, and the abnormal sound evaluation device is operative to evaluate the sound as to whether the sound is abnormal or not based on the digital sound data. Since the sound recording device has the sound data output means for outputting the digital sound data converted from the sound for the abnormal sound evaluation device, the sound recording device and the abnormal sound evaluation device need not be located at a same site. Further, since the abnormal sound evaluation device has the sound data output means for outputting a conclusion of evaluation for the sound recording device, it is possible to check the conclusion of evaluation of a sound at the site where the sound has been recorded even when the sound recording device and the abnormal sound evaluation device are not located at a same site.

Thus, in the case where the equipment is the engine of a vehicle for example, the operator can be informed of a conclusion of evaluation of an abnormal sound even when the vehicle is at a standstill at a site other than the place where the abnormal sound evaluation device is installed, for example, on a highway. As a result, with some conclusions of evaluation, it is possible to proceed with such an operation as repair at that site, hence, take a proper measure promptly.

The conclusion of evaluation includes at least one selected from abnormality information items about presence or absence of an abnormality, a location of the abnormality, an abnormality condition, a replacement part, and a repairing method. With such a construction, even an operator who is not so familiar with abnormal sound evaluation can be informed of the presence or absence of an abnormality, a repairing method and the like based on the information about the evaluation.

A sound recording device according to claim 4 is characterized by comprising sound recording means for recording a sound generated from equipment at a location adjacent the equipment, sound data conversion means for converting the recorded sound into digital sound data, and sound data output means for outputting the digital sound data thus converted for an abnormal sound evaluation device.

An abnormal sound evaluation device according to claim 5 is characterized by comprising: sound data input means for receiving digital sound data converted from a sound generated from equipment and recorded at a location adjacent the equipment; data storage means for storing reference digital sound data corresponding to an abnormal sound generated when an abnormality occurs in the equipment while relating the reference digital sound data to condition data representing a condition of the abnormality; and abnormal sound evaluation means for evaluating the abnormal sound by comparing the digital sound data inputted with the reference digital sound data and outputting a conclusion of the evaluation including abnormality information.

BRIEF DESCRIPTION OF DRAWINGS

FIG. 4 is an illustration of a screen display presenting a conclusion of evaluation according to the same embodiment.

BEST MODE FOR CARRYING OUT THE INVENTION

Hereinafter, one embodiment of the present invention will be described with reference to the drawings.

Figure 1:
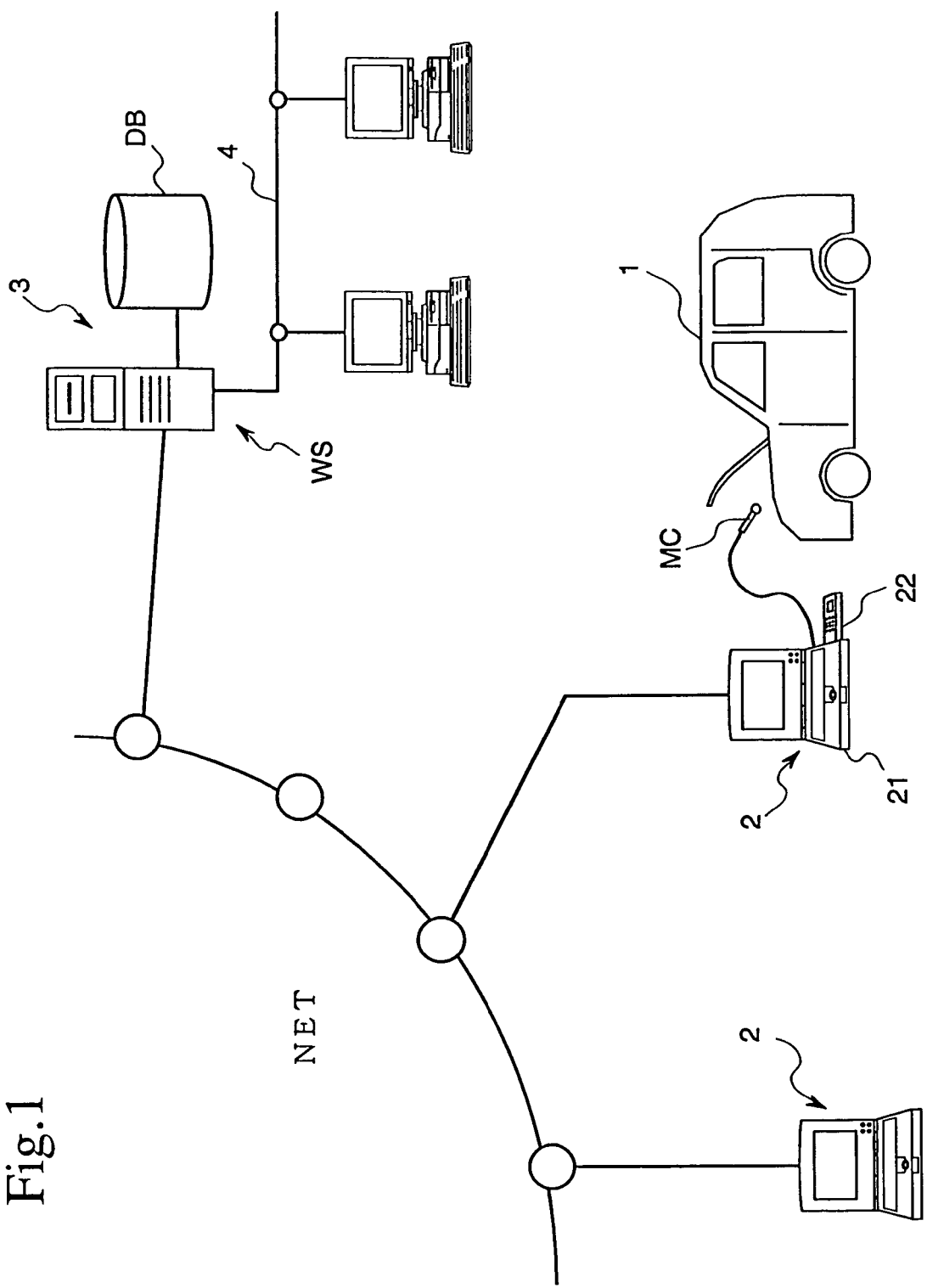
FIG. 1 is a schematic illustration of the configuration of one embodiment according to the present invention.

An abnormal sound evaluation system shown in FIG. 1, which is used for, for example, vehicles as equipment, specifically an automobile 1, comprises a sound recording device 2 for recording sound generated from the automobile 1 at a site where the automobile 1 is located, and an abnormal sound evaluation device 3 installed at, for example, a product control division of an automobile manufacturer for evaluating the sound recorded. In this embodiment, the sound recording device 2 and the abnormal sound evaluation device 3 are connectable to each other via Internet NET as a network for bidirectional communication.

The sound recording device 2 is mainly composed of a microphone MC, a personal computer 21 of a portable type for example (hereinafter referred to as a notebook PC), and a PHS (personal handy phone system) 22 or digital mobile telephone serving as a transmitting/receiving device for transmitting digital sound data to the abnormal sound evaluation device 3 while receiving a conclusion of evaluation outputted from the abnormal sound evaluation device 3. The notebook PC 21 includes an A/D converter for converting an analog signal corresponding to a sound picked up by the microphone MC into digital signal, a storage unit, such as a hard disk, for storing digital signals outputted from the A/D converter, digital sound data prepared from the digital signals, an OS (operating system) and application software, a central processing unit (CPU), a display unit comprising a liquid crystal display panel for visually displaying analog signals, digital data and the like, and an input device including a mouse, a keyboard and the like for entry of information required in recording sound. Further, the notebook PC 21 are preinstalled with sound recording application software (hereinafter referred to as sound recording software) for digital sampling of sounds with high resolution while simultaneously obtaining engine revolution information and the like by executing FFT (fast Fourier transform) for preparing digital sound data from digital signals, Web browser software, and like software. Usually, the notebook PC 21 is equipped with a microphone input terminal and hence allows the microphone MC to input sounds. Thus, sound recording means is realized with the microphone MC and the notebook PC 21, sound conversion means realized with the notebook PC 21, and sound data output means realized with the PHS 22 or digital mobile telephone and the notebook PC 21.

Such a sound recording device 2 is portable and hence is capable of recording sound including an abnormal sound generated from, for example, the engine of the automobile 1 at a site where the automobile 1 is located. Specifically, such sound generated from the engine is recorded by following the procedure: starting-up the sound recording software, converting sound picked up from the engine by the microphone MC into digital sound data on a real time basis, and storing the digital sound data into the storage unit. Thereafter, the digital sound data is outputted, i.e., transmitted to the abnormal sound evaluation device 3 via Internet NET.

The abnormal sound evaluation device 3, which comprises a workstation system WS connected to a LAN (local area network) 4 for example, and a database DB, is operative to evaluate a sound by analyzing digital sound data transmitted from the sound recording device 2 and comparing the digital sound data with reference digital data that has been accumulated in the database DB and then transmit a conclusion of evaluation to the sound recording device 2. The workstation system WS includes a display unit, an input device including a mouse, a keyboard and the like, a central processing unit, a storage unit, and a printer unit and is operative to analyze digital sound data and output the conclusion of evaluation. The workstation system WS has a communication function for transmitting and receiving data via the LAN 4 and Internet NET as well as a database DB management function. The analysis and evaluation of digital sound data are made from various aspects by, for example, a frequency analysis, a spectrum processing based on a high-order algorithm, a frequency analysis with varying number of revolutions, and the like. For such analyses and processing to be achieved, the database DB has accumulation of reference digital sound data to be required in the analyses and processing. Thus, the workstation system WS functions as sound data input means and abnormal sound evaluation means.

The database DB is managed by the workstation system as to input/output of data, retrieval and the like. The database DB has an accumulation of reference digital sound data collected by sampling normal operation sounds of engines and power trains (each including a clutch, transmission, propeller shaft and final reduction gear) under normal operating conditions and abnormal operation sounds of the engines and power trains under abnormal operating conditions on an engine's rpm basis for each vehicle type of automobile 1 in relation to incidental information about vehicle types, engine types, engine loads and the like. The database DB also has an accumulation of conclusions of analyses and evaluations of the aforementioned digital sound data on a reference digital sound data item basis. Such a conclusion of evaluation comprises failure information inclusive of information about the presence or absence of an abnormality, the location of the abnormality, an abnormality condition, a replacement part, and a repairing method. Thus, the database DB functions as data storage means.

Figure 2:
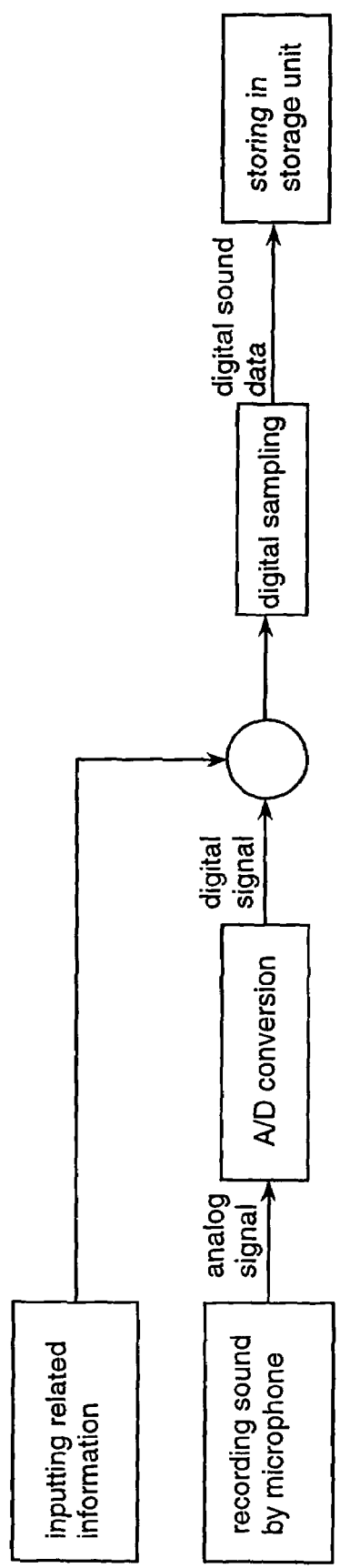
FIG. 2 is a flowchart of a processing procedure in a sound recording device included in the same embodiment.

With such a construction, when automobile 1 calling for a diagnosis as to whether it has a failure or abnormality or not is brought to a car dealer shop for example, the sound recording device 2 records (samples), for example, engine sound of the automobile 1 along with engine revolution information at a location adjacent the automobile 1 in the car dealer shop. In this case, related information including the vehicle type, engine type and the like is inputted by means of the input device. As shown in FIG. 2, an analog signal outputted from the microphone MC is converted into digital sound data by the A/D converter and then temporarily stored in the storage unit together with the related information. In recording the engine sound, the display unit graphically displays the engine sound having been converted into digital sound data in a three-dimensional coordinate system with its axes plotting time, frequency and intensity for example, together with various information incident to the digital sound data in the same screen display. Subsequently, the PHS 22 is connected to the sound recording device 2, which in turn is connected to Internet NET. After the connection with the Internet has been established, the stored digital sound data is transmitted to the abnormal sound evaluation device 3.

Figure 3:
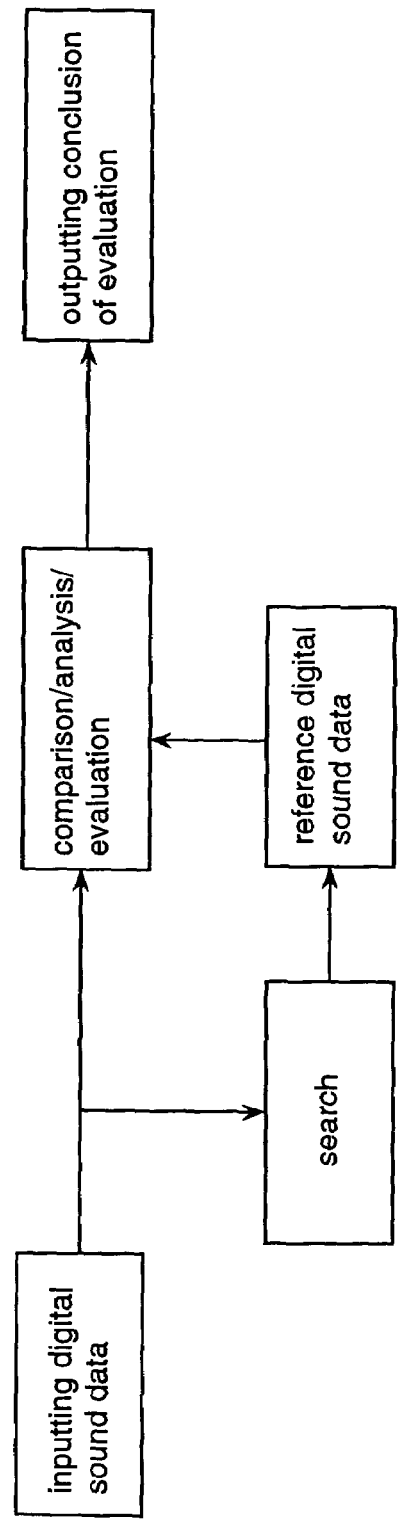
FIG. 3 is a flowchart of a processing procedure in an abnormal sound evaluation device included in the same embodiment.

As shown in FIG. 3, in turn, the abnormal sound evaluation device 3 having received the digital sound data together with the related information and the incidental information via Internet NET searches the database DB based on the information items thus received. Thereafter, the abnormal sound evaluation device 3 analyzes the digital sound data by comparing it with reference digital sound data retrieved from the database DB and evaluates the engine sound recorded based on the conclusion of the comparative analysis. The comparative analysis between the reference digital sound data and the digital sound data is conducted based on differences in frequency, frequency spectrum, waveform and the like when, for example, the numbers of revolutions of the engines are equal to each other. The comparative analysis may be conducted under a condition where the display unit of the workstation system WS displays reference digital sound data and digital sound data corresponding to engine sound recorded to allow the operator to check the data visually. If there is found a difference between the two by the comparative analysis, the abnormal sound evaluation device 3 evaluates the engine sound recorded based on the difference found, prepares a conclusion of evaluation as to whether an abnormality occurs or not, the location of the abnormality, the condition of the abnormality, whether repair is necessary or not, a replacement part to be required in eliminating the abnormality, and the like, and displays the conclusion of evaluation in a screen display shown in FIG. 4 for example. Thereafter, the conclusion of the evaluation thus prepared is outputted to the sound recording device 2 in a state connected to the abnormal sound evaluation device 3 via Internet NET. The conclusion of the evaluation inputted to the sound recording device 2 is visually outputted as displayed by the display unit of the sound recording device 2 in a screen display of the same layout as in the abnormal sound evaluation device 3.

Since the sound recording device 2 is separate from the abnormal sound evaluation device 3 and is composed mainly of the notebook PC 21, the sound recording device 2 is highly convenient for being carried and hence is capable of recording sound generated from the engine of automobile 1 as equipment if it is brought to a site where the automobile 1 to be examined is located, specifically to a car dealer shop for example. This means that the sound recording device 2 is capable of recording sound generated from the engine of automobile 1 regardless of the location of the automobile 1, that is, not only at a car dealer shop but also in the house of the automobile owner or on a highway. Further, since the abnormal sound evaluation device 3 need not be located at the site where the automobile 1 to be examined is located, the abnormal sound evaluation device 3 provided with the database DB exhibits a higher precision of analysis thereby conducting precise evaluation.

Further, since sound generated from the engine can be sampled together with incidental information, converted into digital sound data and promptly transmitted to the abnormal sound evaluation device 3 via Internet NET, the operator is allowed to check whether the automobile 1 before the operator is in a normal condition or an abnormal condition while staying at the car dealer shop, i.e., the site where the engine sound has been recorded. Thus, it is possible to obtain a conclusion of correct evaluation of sound at a site remote from the abnormal sound evaluation device 3 thereby to take a proper measure promptly when an abnormality is found. Since the abnormal sound evaluation device 3 evaluates sound recorded as to whether the sound is normal or abnormal, even those who are not so skilled in the diagnosis of abnormal sound can conduct correct evaluation of sound constantly.

Accordingly, there is no need to borrow automobile 1 from the owner for the purpose of an abnormality or failure checking, so that the burden on the owner can be reduced. Further, since sound can be recorded directly from automobile 1 in which an abnormality occurs, it is possible to eliminate such an operation as to reproduce an abnormal condition using another automobile 1 of the same type. Therefore, the abnormal sound evaluation system can record and evaluate a sound generated from the automobile 1 in question under an abnormal condition upon the occurrence of an abnormality, thereby offering evaluation of higher accuracy.

It should be note that the present invention is not limited to the foregoing embodiment.

While the embodiment having been described above uses a PHS in connecting the sound recording device 2 to Internet NET, it is possible to connect the sound recording device 2 to Internet NET by interconnecting a modular jack of a modem incorporated in the notebook PC 21 for example and a modular jack provided indoors or of a public telephone through a cable.

It is possible to provide a plurality of sound recording devices 2 for respective sound recording sites. In this case, if the sound recording devices 2 establish connection with Internet NET at the same time, the abnormal sound evaluation device 3 analyzes and evaluates digital sound data items in the order of their inputting from earliest occurrence to latest occurrence. Thus, even when plural sound recording devices 2 are working, the sole abnormal sound evaluation device 3 can achieve evaluation of sounds recorded by respective sound recording devices 2. By thus using plural sound recording devices 2 in the system, it is possible to reduce the cost to be incurred for the whole system as well as to detect and evaluate multiplicity of abnormalities or failures at substantially the same time.

The abnormal sound evaluation system may be configured to be capable of recording sounds generated indoors of an automobile during traveling of the automobile.

The present invention is not limited to the features of different parts of the system shown in the drawings and may be modified variously without departing from the spirit and scope of the present invention.

INDUSTRIAL APPLICABILITY

According to the present invention having been described above, the sound recording device has the sound data output means for outputting digital sound data converted from a sound for the abnormal sound evaluation device and is operative to record the sound, convert the recorded sound into digital sound data and input the converted digital sound data to the abnormal sound evaluation device, and the abnormal sound evaluation device is operative to evaluate the sound as to whether the sound is abnormal or not based on the digital sound data. With this construction, it is possible to evaluate a sound even when the sound recording device and the abnormal sound evaluation device are not located at a same site.

Thus, in the case where the equipment is the engine of a vehicle for example, it is possible to evaluate an abnormal sound even when the vehicle is at a standstill at a site other than the place where the abnormal sound evaluation device is installed, for example, on a highway. Further, since the abnormal sound evaluation device is capable of receiving digital sound data from plural sound recording devices, it is possible to avoid redundancy of functions thereby to reduce the cost to be incurred for the system as a whole.

In the invention according to claim 2, the sound recording device has the sound data output means for outputting digital sound data converted from a sound for the abnormal sound evaluation device and, therefore, it is possible to evaluate the sound even when the sound recording device and the abnormal sound evaluation device are not located at a same site. Further, since the abnormal sound evaluation device has the sound data output means for outputting a conclusion of evaluation for the sound recording device, it is possible to check the conclusion of evaluation of the sound at the site where the sound has been recorded even when the sound recording device and the abnormal sound evaluation device are not located at a same site.

Thus, in the case where the equipment is the engine of a vehicle for example, the operator can be informed of a conclusion of evaluation of an abnormal sound even when the vehicle is at a standstill at a site other than the place where the abnormal sound evaluation device is installed, for example, on a highway. As a result, with some conclusions of evaluation, it is possible to proceed with such an operation as repair at that site, hence, take a proper measure promptly.

The invention claimed is:

1. An abnormal sound evaluation system comprising a portable sound recording device for recording a sound generated from a component in a vehicle at a location adjacent the component, and an abnormal sound evaluation device for evaluating the sound recorded, wherein:

the portable sound recording device includes sound data conversion means for converting the recorded sound into digital sound data, and sound data output means for outputting the digital sound data thus converted for the abnormal sound evaluation device;

the abnormal sound evaluation device includes sound data input means for receiving the digital sound data, and abnormal sound evaluation means for evaluating the sound as to abnormality based on the digital sound data inputted and outputting a conclusion of the evaluation including abnormality information about the component; and the abnormal sound evaluation device comprises data storage means for storing reference digital sound data corresponding to an abnormal sound generated when an abnormality occurs in the component in relation to incidental information about an abnormality condition;

wherein the portable sound recording means is used at a site other than where the abnormal sound evaluation device is located, and the portable sound recording means and abnormal sound evaluation device are connectable to each other for bidirectional communication.

2. The abnormal sound evaluation system according to claim 1, wherein the conclusion of the evaluation includes at least one selected from abnormality information items about presence or absence of an abnormality, a location of the abnormality, an abnormality condition, a replacement part, and a repairing method.

3. The abnormal sound evaluation system according to claim 1, wherein the component is an engine and the portable sound recording device records a sound generated from the engine with engine revolution information.

4. An abnormal sound evaluation system comprising a portable sound recording device for recording a sound generated from a component in a vehicle at a location adjacent the component, and an abnormal sound evaluation device for evaluating the sound recorded, wherein:

the portable sound recording device includes sound data conversion means for converting the recorded sound into digital sound data, sound data output means for outputting the digital sound data thus converted for the abnormal sound evaluation device, and evaluation conclusion input means for receiving a conclusion of evaluation outputted from the abnormal sound evaluation device; and the abnormal sound evaluation device includes sound data input means for receiving the digital sound data outputted from the portable sound recording device, abnormal sound evaluation means for evaluating the sound based on the digital sound data inputted and outputting a conclusion of the evaluation including abnormality information, and evaluation conclusion output means for outputting the conclusion of the evaluation outputted by the abnormal sound evaluation means for the portable sound recording device;

the abnormal sound evaluation device comprises data storage means for storing reference digital sound data corresponding to an abnormal sound generated when an abnormality occurs in the component in relation to incidental information about an abnormality condition;

wherein the portable sound recording means is used at a site other than where the abnormal sound evaluation device is located, and the portable sound recording means and abnormal sound evaluation device are connectable to each other for bidirectional communication.

5. The abnormal sound evaluation system according to claim 4, wherein the conclusion of the evaluation includes at least one selected from abnormality information items about presence or absence of an abnormality, a location of the abnormality, an abnormality condition, a replacement part, and a repairing method.

6. The abnormal sound evaluation system according to claim 4, wherein the component is an engine and wherein the portable sound recording device records a sound generated from the engine with engine revolution information.

7. An abnormal sound evaluation device comprising:

sound data input means for receiving digital sound data converted from a sound generated from a component in a vehicle and recorded at a location adjacent the component;

data storage means for storing reference digital sound data corresponding to an abnormal sound generated when an abnormality occurs in the component while relating the reference digital sound data to condition data representing a condition of the abnormality; and abnormal sound evaluation means for evaluating the abnormal sound by comparing the digital sound data inputted with the reference digital sound data and outputting a conclusion of the evaluation including abnormality information wherein the abnormal sound evaluation device is installed at a site other than the location of the vehicle, and the portable sound recording means and abnormal sound evaluation device are connectable to each other for bidirectional communication.

8. The abnormal sound evaluation device according to claim 7, wherein the conclusion of the evaluation includes at least one selected from abnormality information items about presence or absence of an abnormality, a location of the abnormality, an abnormality condition, a replacement part, and a repairing method.

9. The abnormal sound evaluation device according to claim 7, wherein the component is an engine, wherein the recorded sound is a sound generated from the engine and the sound generated from the engine is recorded with engine revolution information.

* * * * *